(12) United States Patent
Kolobow et al.

(10) Patent No.: US 7,503,328 B2
(45) Date of Patent: Mar. 17, 2009

(54) MUCUS SLURPING ENDOTRACHEAL TUBE

(75) Inventors: Theodor Kolobow, Rockville, MD (US); Gianluigi Li Bassi, Bethesda, MD (US); Francesco Curto, Bethesda, MD (US)

(73) Assignee: The United States of America as represented by the Secretary of The Department of Health and Human Services, Washington, DC (US)

( * ) Notice: Subject to any disclaimer, the term of this patent is extended or adjusted under 35 U.S.C. 154(b) by 0 days.

(21) Appl. No.: 11/081,420

(22) Filed: Mar. 15, 2005

(65) Prior Publication Data

US 2006/0207602 A1 Sep. 21, 2006

(51) Int. Cl.
*A61M 16/00* (2006.01)
*A62B 9/06* (2006.01)

(52) U.S. Cl. .............. 128/207.14; 128/200.26; 128/207.15; 128/207.16; 604/93.01

(58) Field of Classification Search ............ 128/207.14, 128/207.15, 207.16, 200.26; 604/93.01
See application file for complete search history.

(56) References Cited

U.S. PATENT DOCUMENTS

| | | | |
|---|---|---|---|
| 3,376,863 A | 4/1968 | Kolobow | |
| 3,463,728 A | 8/1969 | Kolobow | |
| 3,489,647 A | 1/1970 | Kolobow | |
| 3,788,326 A * | 1/1974 | Jacobs | 128/207.15 |
| 3,969,240 A | 7/1976 | Kolobow | |
| 4,093,515 A | 6/1978 | Kolobow | |
| 4,116,201 A | 9/1978 | Shah | |
| 4,305,392 A * | 12/1981 | Chester | 604/98.01 |
| 4,356,958 A | 11/1982 | Kolobow et al. | |

(Continued)

FOREIGN PATENT DOCUMENTS

WO   WO 2005/009522   *  2/2005

(Continued)

OTHER PUBLICATIONS

PCT International Searching Authority [PCT/US2006/009166], dated Mar. 7, 2006 (5 pages).

*Primary Examiner*—Patricia M Bianco
*Assistant Examiner*—Nihir Patel
(74) *Attorney, Agent, or Firm*—Townsend and Townsend and Crew LLP; Guy W. Chambers

(57) ABSTRACT

An endotracheal tube assembly (10) is disclosed which suctions away bacteria multiplying mucus before such mucus can accumulate on the inside walls of the endotracheal tube (14). In the preferred embodiment, one or more suctioning tubes (20, 21) are formed into the walls of an endotracheal tube so that they extend along length of the endotracheal tube. A plurality of mucus slurping holes (34) are then formed at or near the distal end of the endotracheal tube and connected to the suctioning tubes. In operation, suctioning through the mucus slurping holes is preferably performed intermittently during patient expiration. By timing this intermittent suctioning with patient expiration, the suctioning flow will be in the same direction as patient breathing. While the mucus slurper of the present invention has been found to be effective at keeping the inner walls of the endotracheal tube free of mucus deposits, it can nonetheless be combined with other cleaning and disinfectant techniques for greater assurance of cleanliness.

3 Claims, 4 Drawing Sheets

U.S. PATENT DOCUMENTS

| | | | |
|---|---|---|---|
| 4,419,089 A | 12/1983 | Kolobow et al. | |
| 4,446,864 A * | 5/1984 | Watson et al. | 128/207.14 |
| 4,525,166 A * | 6/1985 | Leclerc | 604/133 |
| 4,551,251 A | 11/1985 | Kolobow et al. | |
| 4,607,635 A | 8/1986 | Heyden | |
| 4,637,389 A * | 1/1987 | Heyden | 128/207.15 |
| 4,688,568 A * | 8/1987 | Frass et al. | 128/207.15 |
| 4,739,756 A | 4/1988 | Horn | |
| 4,813,931 A * | 3/1989 | Hauze | 604/540 |
| 4,889,137 A | 12/1989 | Kolobow | |
| 5,029,580 A | 7/1991 | Radford et al. | |
| 5,186,167 A | 2/1993 | Kolobow | |
| 5,255,675 A | 10/1993 | Kolobow | |
| 5,305,740 A | 4/1994 | Kolobow | |
| 5,347,991 A * | 9/1994 | Nakao et al. | 600/156 |
| 5,363,860 A * | 11/1994 | Nakao et al. | 600/573 |
| 5,364,358 A | 11/1994 | Hewitt et al. | |
| 5,429,127 A | 7/1995 | Kolobow | |
| 5,537,729 A | 7/1996 | Kolobow | |
| 5,687,714 A | 11/1997 | Kolobow et al. | |
| 5,709,691 A | 1/1998 | Morejon | |
| 5,711,296 A | 1/1998 | Kolobow | |
| 5,722,395 A | 3/1998 | Kolobow | |
| 5,785,998 A | 7/1998 | Kolobow | |
| 5,819,723 A * | 10/1998 | Joseph | 128/207.14 |
| 5,819,727 A * | 10/1998 | Linder | 128/200.26 |
| 5,832,920 A * | 11/1998 | Field | 128/207.14 |
| 6,027,516 A | 2/2000 | Kolobow et al. | |
| 6,082,361 A | 7/2000 | Morejon | |
| 6,254,591 B1 * | 7/2001 | Roberson | 604/541 |
| 6,318,368 B1 | 11/2001 | Morejon | |
| 6,460,540 B1 | 10/2002 | Klepper | |
| 6,494,208 B1 | 12/2002 | Morejon | |
| 6,655,382 B1 | 12/2003 | Kolobow | |
| 6,679,262 B1 | 1/2004 | Mroejon | |
| 6,725,862 B2 * | 4/2004 | Klinberg et al. | 128/207.14 |
| 7,051,737 B2 | 5/2006 | Kolobow et al. | |
| 2003/0145860 A1 | 8/2003 | Johnson | |
| 2004/0249337 A1 * | 12/2004 | DiFiore | 604/40 |
| 2005/0022809 A1 | 2/2005 | Wondka | |

FOREIGN PATENT DOCUMENTS

| | | | |
|---|---|---|---|
| WO | WO 2005/009522 A1 | 2/2005 | |

* cited by examiner

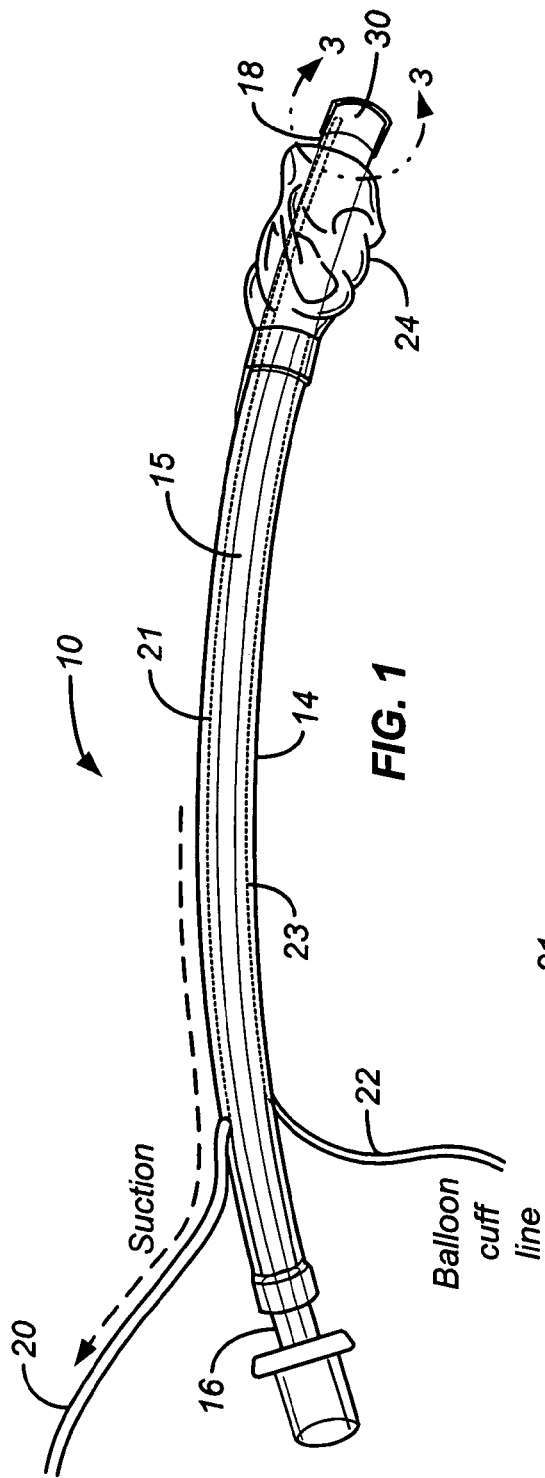
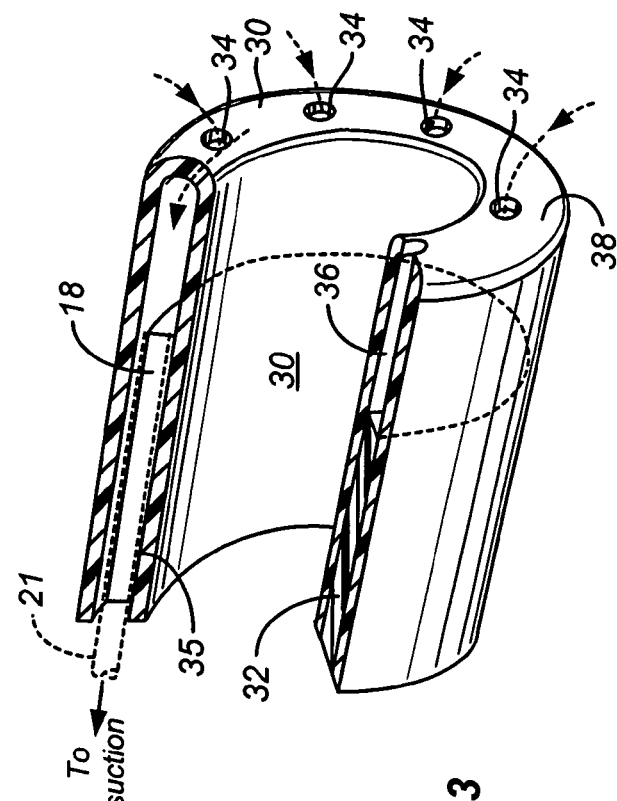
FIG. 1
FIG. 3

MUCUS SLURPING ENDOTRACHEAL TUBE

TECHNICAL FIELD OF THE INVENTION

The present invention relates to the cleaning of medical devices used to assist breathing. More particularly, mucus slurping holes are formed at or near the distal end of an endotracheal tube to evacuate mucus before it can migrate up onto the inner walls of the endotracheal tube.

BACKGROUND OF THE INVENTION

Through injury or diseases, human or animal lungs can become too weak to sustain a sufficient flow of oxygen to the body and to remove adequate amounts of expired carbon dioxide. Under these circumstances, it is often necessary to aid the lungs through forms of mechanical assistance, such as mechanical ventilation.

In a common form, mechanical ventilation involves the introduction of an endotracheal tube and, in some cases, a small, open-ended catheter within that tube, into the trachea of a human or animal. The distal ends of the endotracheal tube and/or catheter are positioned to rest at or slightly above the carina of the lungs. A well-humidified oxygen/air mixture is then introduced through the endotracheal tube and/or catheter to provide oxygen to the lungs. In less severe circumstances, the oxygen/air mixture can be supplied through the endotracheal tube and/or catheter using continuous positive airway pressure (CPAP). Where CPAP is used, the patient will use his or her own lung power to exhale the inspired gas. In more severe circumstances, it is necessary to use mechanically controlled ventilation with a positive end expiratory pressure (PEEP).

One problem commonly associated with the use of endotracheal tubes is the accumulation of mucus on the inside walls of the endotracheal tube. In a healthy human, mucus is secreted through glandular action in the trachea/bronchial tree and is progressively transported upward through the action of cilia along the tracheal airways. Upon nearing the vocal folds, such mucus is either swallowed or expectorated.

This mucus transport mechanism is generally not available, though, to a patient intubated with an endotracheal tube. Typically, the endotracheal tube will block the mucus clearing action of the adjacent cilia, particularly where an inflatable cuff is used to firmly position the endotracheal tube against the inside wall of the trachea. In such case, instead of being expelled from the lungs and trachea, the mucus will tend to migrate up from the bronchia tree through the distal end of the endotracheal tube and then collect on the inside walls of the endotracheal tube. If such mucus collection is allowed to continue, the internal diameter of the endotracheal tube will become smaller, which makes it more difficult to breathe. Perhaps more seriously, infectious bacteria (e.g., *Staph* and *Pseudomonas* spp.) tend to grow and multiply on the stagnant mucus. The bacteria infected mucus can then aerosolize and deposit into the patient's lungs, leading to ventilator-associated pneumonia.

A number of approaches have been developed to address the mucus accumulation problem for endotracheal tubes. In the most basic approach, the mucus laden endotracheal tube is simply removed from the patient's trachea and replaced with a clean endotracheal tube. Needless to say, removing the mucus laden endotracheal tube is very uncomfortable for patient, particularly since ventilation must be interrupted during the removal process. Moreover, reinsertion of a clean endotracheal tube can lead to tracheal injury, particularly if it is done frequently.

In another common approach, salt water is introduced into the endotracheal tube to dissolve the mucus and a suction catheter is then inserted into the endotracheal tube to try to vacuum up the dissolved mucus deposits. This suctioning approach has a number of drawbacks. First of all, the suctioning process typically takes 10 to 15 seconds to complete, which can seem like an agonizingly long time for many patients. Secondly, the suction catheter tends to miss a number of the accumulated mucus deposits and thereby leaves them as a breeding ground for infectious bacteria.

A further approach to the mucus accumulation problem is described in the lead inventor's U.S. Pat. No. 5,687,714. In this approach, droplets of water or saline are entrained in the oxygen/air ventilation mixture to continually dissolve mucus before it has an opportunity to form deposits and a reverse thrust catheter is used to help transport dissolved mucus away from the lungs.

Recently, the lead inventor has developed a mucus shaver cleaning apparatus which is described in co-pending patent application Ser. No. 10/773,570, the disclosure of which is hereby incorporated by reference. This mucus shaver cleaning apparatus comprises a central flexible tube with an inflatable balloon at its distal end. Affixed to the inflatable balloon are one or more shaving rings, each having a squared leading edge to shave away mucus accumulations. In operation, the uninflated cleaning apparatus is inserted into the endotracheal tube until its distal end is properly aligned with or slightly beyond the distal end of the endotracheal tube. After proper alignment, the balloon is inflated by a suitable inflation device, such as a syringe, until the balloon's shaving rings are pressed against the inside surface of the endotracheal tube. The cleaning apparatus is then pulled out of the endotracheal tube and, in the process, the balloon's shaving rings shave off the mucus deposits from the inside of the endotracheal tube.

BRIEF SUMMARY OF THE INVENTION

The present invention provides a suctioning assembly built into an endotracheal tube which removes mucus before it accumulates on the inside walls of the endotracheal tube. In the preferred embodiment, one or more suctioning tubes are formed into the walls of an endotracheal tube so that they extend along the length of the endotracheal tube. A plurality of mucus slurping holes are formed at or near the distal end of the endotracheal tube and connected to the suctioning tube(s). When a single suctioning tube is formed in the endotracheal tube walls, the mucus slurping holes are preferably formed at the distal end of a cap which is fused onto the distal end of the endotracheal tube. An annular space is left between the distal end of the cap and the distal end of the endotracheal tube so that the endotracheal tube suction tube can create suction throughout all of the cap's mucus slurping holes. When multiple suctioning tubes are formed in the endotracheal tube walls, each of those suctioning tubes preferably connects to a single corresponding slurping hole at the distal end of the endotracheal tube. In this multiple suctioning tube embodiment, there is no need to fit a cap onto the distal end of the endotracheal tube.

In operation, suctioning through the mucus slurping holes is preferably performed intermittently during patient expiration, rather than continuously. By timing this intermittent suctioning with patient expiration, the suctioning flow will be in the same direction as patient breathing (i.e., outward) and will be in operation when mucus is most likely to migrate into the endotracheal tube. In order to time the slurping operation to correspond with patient expiration, a pressure transducer is preferably attached to the mechanical ventilator to sense a drop in positive airway pressure associated with patient expiration. When such a pressure drop is sensed, the pressure transducer sends a signal to an electronic synchronizer to open a synchronized valve. When the synchronized valve is opened, vacuum is applied to the suctioning line so that mucus can be slurped up through the mucus slurping holes of the endotracheal tube. Vials are provided externally in the suctioning line to accumulate mucus secretions and condensation before such secretions and condensation can foul the synchronized valve. After a predetermined time or a sufficient rise in mechanical ventilator pressure is sensed, suction pressure to the mucus slurping holes is turned off and the patient is allowed to inhale humidified air without any suctioning interference.

While the mucus slurper of the present invention has been found to be effective at keeping the inner walls of the endotracheal tube free of mucus deposits, it can nonetheless be combined with other cleaning and disinfectant techniques for greater assurance of cleanliness. For example, the mucus shaver described in co-pending patent application Ser. No. 10/773,570 can be periodically used to remove any mucus deposits which might somehow evade the mucus slurper. Also, the inside walls of the endotracheal tube can be coated with a bactericidal film to kill any potentially harmful bacteria which comes into contact with those inside walls.

BRIEF DESCRIPTION OF THE DRAWINGS

FIG. 1 shows a side view of a mucus slurping endotracheal tube assembly of the present invention incorporating a single suctioning line and a distal end cap with mucus slurping holes.

FIG. 3 shows a close-up perspective view of the distal end cap with mucus slurping holes of FIG. 1 fitted onto the distal end of the endotracheal tube.

DETAILED DESCRIPTION OF THE INVENTION

Figure 2:
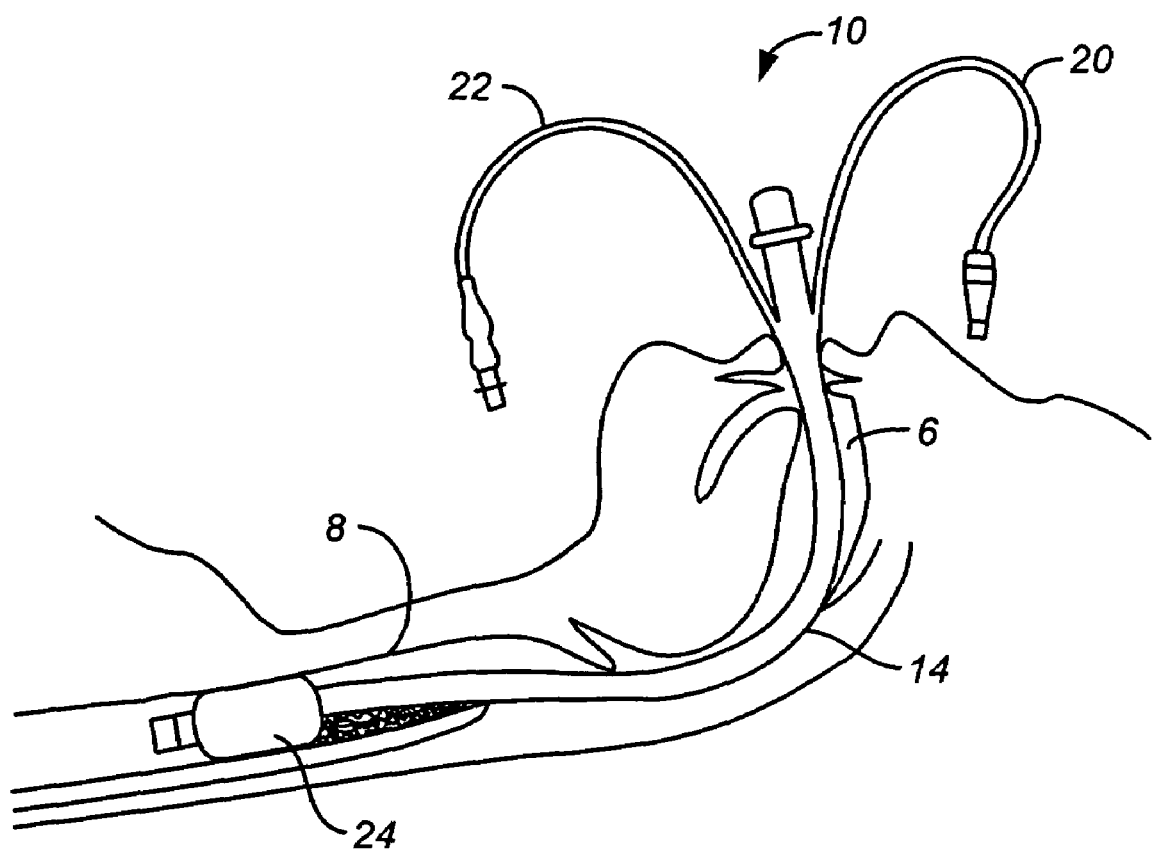
FIG. 2 shows a cut-away view of how a mucus slurping endotracheal tube would appear after being inserted into a patient's trachea.

Referring now to FIG. 1, a preferred form of mucus slurping endotracheal tube assembly 10 is shown. This endotracheal tube assembly 10 includes an endotracheal tube 14 having tubular walls 15, a proximal end 16 and a distal end 18, an external suctioning tube 20, an internal suctioning tube 21, an external balloon cuff inflation tube 22, an internal balloon cuff inflation tube 23, a balloon cuff 24 and a mucus slurping cap 30. The endotracheal tube 14 is preferably formed of a flexible medical plastic, such as polyvinylchloride (PVC) or silicone rubber, and is narrow enough in outside diameter that it can be comfortably inserted into a patient's trachea until its distal end 18 reaches a point which is slightly above the carina of the lungs. The patient can be either an animal or a human. FIG. 2 illustrates how the endotracheal tube 14 of the present invention can be inserted through a patient's mouth 6 and into a patient's trachea 8 so that the exposed ends of the external suctioning tube 20 and external balloon cuff inflation tube 22 remain outside the patient's mouth 6.

After the endotracheal tube is inserted into the patient's trachea 8, the uninflated balloon cuff 24 is preferably inflated with air or fluid using balloon cuff inflation tubes 22, 23, until the balloon cuff 24 snugly presses against the patient's trachea 8 (see, FIG. 2). Inflation of the balloon cuff 24 using the balloon cuff inflation tubes 22, 23 allows the endotracheal tube 14 to remain correctly positioned within the patient's trachea despite vibration or other disturbances.

Like the external balloon cuff inflation tube 22, the external suctioning tube 20 also enters the endotracheal tube 14 near its proximal end 16. Also like the external balloon cuff inflation tube 22, the external suctioning tube 20 connects to a tube 21 inside the endotracheal tube walls. Unlike the internal balloon cuff inflation tube 22, though, the internal suctioning tube 21 terminates at the distal end 18 of the endotracheal tube.

As shown more clearly in FIG. 3, a mucus slurping cap 30 can be fused onto the distal end 18 of the endotracheal tube 14 shown in FIG. 1. The mucus slurping cap 30 is formed with an annular space 32 which allows the cap 30 to be snugly fused around the distal end 18 of the endotracheal tube 14. The purpose of the mucus slurping cap 30 is to allow mucus to be suctioned into holes 34 of the mucus slurping cap 30 and into the internal suctioning line 21 so that mucus will not collect on the inside wall 35 of endotracheal tube 14. The holes 34 in mucus slurping cap are preferably small in diameter (e.g., less than 1 millimeter) and preferably number between 2 and 8. In the preferred embodiment, the mucus slurping cap holes 34 are at the distal end of the cap and face downward toward the patient's lungs. Alternatively, the mucus slurping cap holes may be very near the distal end of the cap (e.g., 0.5 to 3.0 cm from the distal end) and face inwardly or a combination of downwardly and inwardly. To allow suction to be applied through all of the mucus slurping holes 34, an annular gap 36 is preferably left in the mucus slurping cap 30 between the distal end 18 of the endotracheal tube and the distal end 38 of the mucus slurping cap 30. The length of this annular gap 36 can be as small as 2 to 3 millimeters. This annular gap 36 allows suction airflow from suctioning tube 21 to be spread throughout the entire distal end 38 of the mucus slurping cap 30.

For the present invention, a Hi-Lo® continuous aspiration of subglottic secretions ("CASS") endotracheal tube manufactured by Mallinckrodt, Inc. of St. Louis, Mo. is a advantageous choice for an endotracheal tube assembly 10 of the type shown in FIG. 1. The Mallinckrodt CASS tube includes both suctioning and balloon cuff inflation tubes. In contrast to the present invention, though, the suctioning tube of the Mallinckrodt CASS endotracheal tube is blocked off above the balloon cuff and connected to a relatively large hole formed in the endotracheal tube wall above the balloon cuff to suction away any saliva which drips down the inside wall of the endotracheal tube. In order to modify the Mallinckrodt CASS tube for the present invention, Mallinckrodt's saliva suctioning hole is blocked and the distal end of Mallinckrodt's suctioning tube is unblocked so that Mallinckrodt's suction tube extends all the way to the distal end of the endotracheal tube. A mating mucus slurping cap, of the type shown in FIG. 3, is then attached to the distal end of Mallinckrodt's CASS tube to form the type of mucus slurping endotracheal tube assembly shown in FIG. 1.

Figure 4:
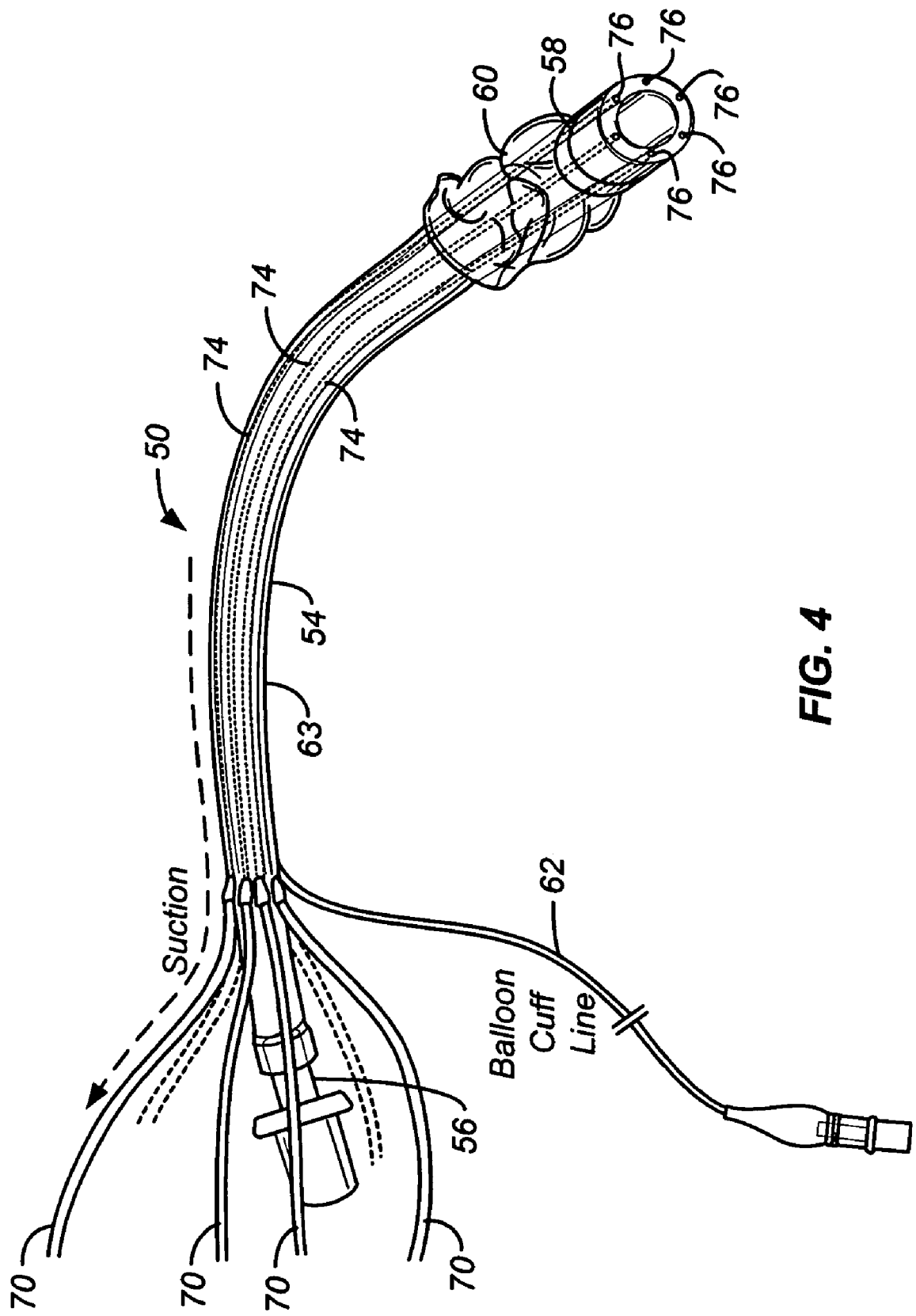
FIG. 4 shows a shows a side view of a mucus slurping endotracheal tube of the present invention incorporating multiple suctioning lines leading to multiple mucus slurping holes.

An alternative form of mucus slurping endotracheal tube assembly 50 is shown in FIG. 4. Like the endotracheal tube assembly 10 shown in FIG. 1, this alternative endotracheal tube assembly 50 includes an endotracheal tube 54 having proximal 56 and distal 58 ends as well as a balloon cuff 60 and balloon cuff inflation tubes 62, 63. This alternative endotracheal tube assembly 50 differs from the endotracheal tube assembly 10 shown in FIG. 1 insofar as there are multiple external and internal suctioning tubes 70, 74. The external suctioning tubes 70 are connected to the endotracheal tube assembly 50 at a point near the proximal end 56 of the endotracheal tube 54 so as to be positioned outside the patient's mouth 6 during use (see, FIG. 2). Each of these external suctioning tubes 70 then continues on as interior suctioning tubes 74 inside the walls of the endotracheal tube 54 until they terminate as mucus slurping holes 76 at the distal end 58 of the endotracheal tube 54. As in the FIG. 1 embodiment, these mucus slurping holes 76 are preferably at the distal end of the endotracheal tube assembly 50 and face downward toward the patient's lungs, but may alternatively face inward or a combination of downward and inward. In this FIG. 4 embodiment, there is a one-to-one correspondence between suctioning tubes 70, 74 and mucus slurping holes 76 so that there is no need to include a mucus slurping cap 30 to distribute suction pressure from one suction line into a plurality of mucus slurping holes as in the FIG. 1 embodiment.

In operation, suctioning through the mucus slurping holes is preferably accomplished intermittently during patient expiration. By timing the mucus slurping suctioning with the patient's expiration, the flow of suctioned air moves in the same direction as the ventilated air (i.e., outward). By avoiding suctioning during patient inhalation, there in no interference with the patient's efforts to inhale ventilated air.

Figure 5:
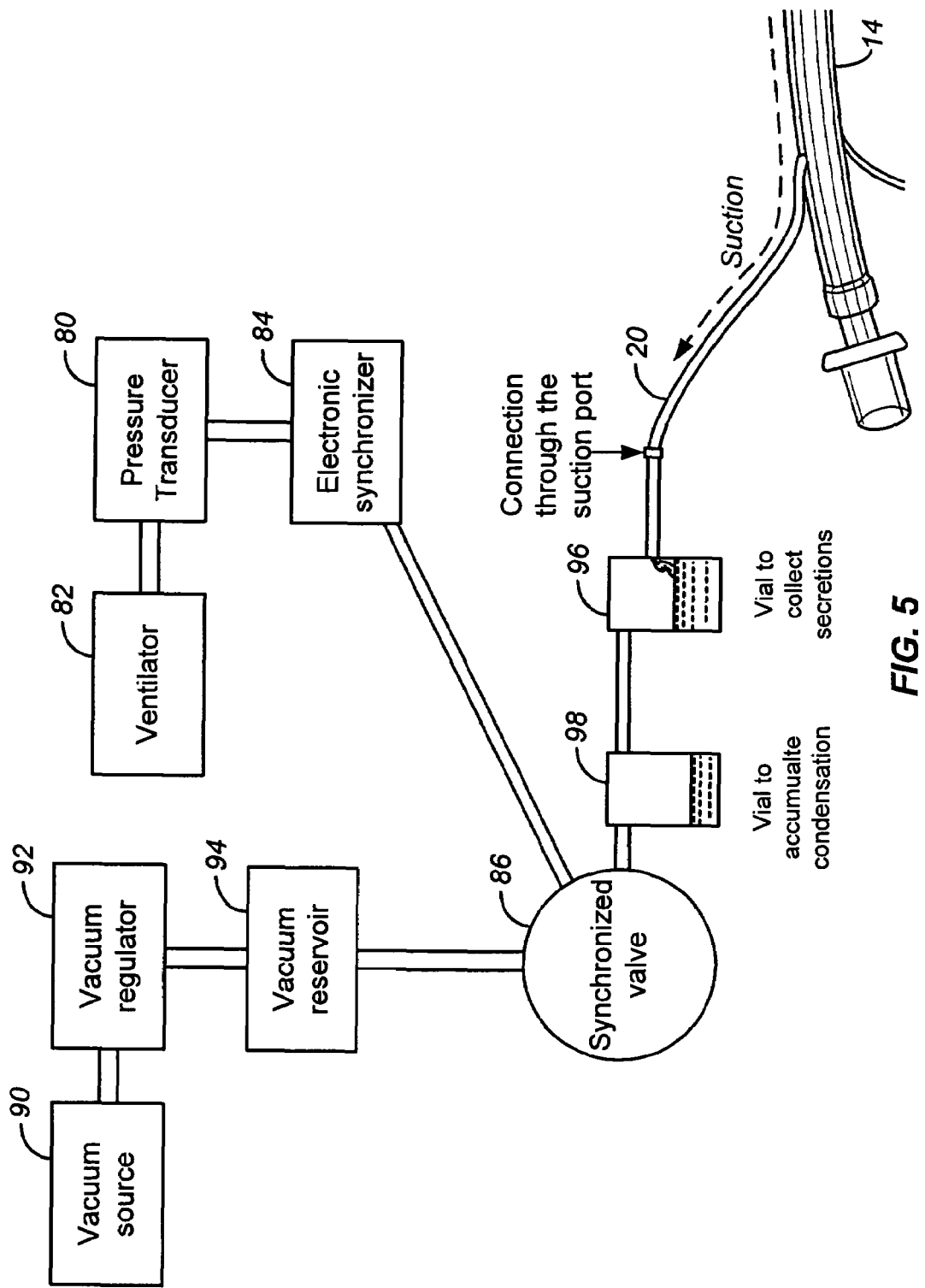
FIG. 5 shows a schematic of the synchronization and suctioning equipment which allows mucus slurping to be intermittently activated during patient expiration.

FIG. 5 illustrates the equipment which can be used to time the mucus slurping with the patient expiratory phase. In the preferred embodiment, a pressure transducer 80 measures the airway pressure produced by the mechanical ventilator 82. When the pressure transducer 80 measures a sufficient drop in positive airway pressure or a negative airway pressure, the pressure transducer 80 interprets this as corresponding to a patient expiratory phase and, accordingly, sends an activation signal to electronic synchronizer 84. The inventors have found that a sufficient drop in positive airway pressure to trigger the electronic synchronizer can be a drop of twenty-five percent (25%) from the peak positive airway pressure. The electronic synchronizer 84 will then use the activation signals from pressure transducer 80 to open the synchronized valve 86 at a predetermined frequency.

The inventors have found that mucus slurping suction does not need to be applied during every patient expiration. Satisfactory results have been achieved, for example, when suctioning is applied only once during every thirty breaths. Preferably, the frequency of mucus slurping suctioning ranges from once every half minute to once every 7 minutes. Further, the mucus slurping suctioning need not be of lengthy duration. Satisfactory results can be achieved with suctioning cycles lasting as short as half of a second.

When the synchronized valve 86 is opened by the electronic synchronizer 84, suctioning or vacuum is applied to suctioning tube 20 by vacuum source 90. The strength of the suction is regulated by vacuum regulator 92 in conjunction with vacuum reservoir 94. Preferably, the applied vacuum is between 300 to 500 mm Hg. As mucus is drawn away from the endotracheal tube through suctioning tube 20, the mucus will pass into a secretion collection vial 96 for collection and later disposal. The suctioning tube 20 then preferably passes through a condensation accumulation vial 98 before it reaches the synchronized valve 86. The condensation accumulation vial 98 removes vapor from the suctioned gas. Through use of vials 96, 98, a sufficient amount of mucus and vapor will be removed from the suctioned gases to prevent fouling of the synchronized valve 86 and vacuum equipment 90, 92, 94.

For best results, the patient is preferably in a position where both the endotracheal tube and patient's neck are at or below horizontal. By having the neck at or below the level of the lower body, any mucus which migrates up from the lungs and is able to evade the mucus slurping action of the present invention will continue to migrate up the endotracheal tube and out of the patient's mouth. Nonetheless, while it is preferred to have the patient's neck at or below horizontal, the mucus slurping endotracheal tube of the present invention can still be helpful in preventing the accumulation of mucus on the inside walls of an endotracheal tube even if the upper body is in an elevated position.

Similarly, while it is preferred that mucus slurping take place during patient expiration, the mucus slurping function of the present invention may also prove valuable when there is continuous positive airway pressure (CPAP) or where patient expiration cannot be easily detected. If the mucus slurping function is activated without being timed to patient expiration, greater care should be taken in setting the suction pressure and duration of the mucus slurping. For example, a high suction pressure for mucus slurping would not be advisable while the patient is trying to inhale ventilated air.

The mucus slurping endotracheal tube of the present invention can advantageously be used with other mucus clearing or bacteria destroying techniques. For example, the mucus shaver cleaning apparatus of co-pending patent application Ser. No. 10/773,570 can be periodically used to shave off any mucus which is able to work its way into the endotracheal tube by evading the mucus slurping action of the present invention. Nonetheless, because of the presence of mucus slurping action, the mucus shaver cleaning apparatus would need to be used less frequently if it is combined with the present invention. Similarly, the present invention can be used with an endotracheal tube whose inside walls are coated with a bactericidal film, such as a silver-sulfadiazine ("SSD") film, a chlorhexidine ("CHD") film, a film combining SSD with CHD and/or a film with oligodynamic iontophoretic materials (e.g., silver, platinum and/or carbon in a polyurethane solution). To the extent that any mucus is able to evade the mucus slurping action of the present invention, a bactericidal film can prevent harmful bacteria from growing on such mucus.

EXAMPLE I

The mucus slurping endotracheal tube of the present invention was tested with healthy, anesthetized and paralyzed sheep. A Mallinckrodt CASS tube was modified and fitted with a mucus slurping cap in the manner illustrated in FIG. 1 and then inserted into the trachea of the anesthetized sheep. The anesthetized sheep were mechanically ventilated for 72 hours with mucus periodically being suctioned through the mucus slurping cap. No other device was used to assist in the cleaning of mucus from the inside walls of the endotracheal tube. At the end of the 72 hour study, the sheep were euthanized and autopsied.

After removal and inspection of the modified endotracheal tube, no trace of mucus was found throughout the length of the endotracheal tube. No gross abnormalities of the tracheal mucosa were seen in the autopsied sheep. Bacterial cultures of the 5 lobes of the autopsied sheep lungs were negative. Arterial blood gases were within normal range.

In the foregoing specification, the invention has been described with reference to specific preferred embodiments and methods. It will, however, be evident to those of skill in the art that various modifications and changes may be made without departing from the broader spirit and scope of the invention as set forth in the appended claims. Accordingly, the specification and drawings are to be regarded in an illustrative, rather than restrictive, sense; the invention being limited only by the appended claims.

What is claimed is:

1. A mucus cleaning endotracheal tube apparatus comprising:
    an endotracheal tube having tubular walls, a proximal end and a distal end;
    a suctioning tube within said endotracheal tube walls extending from approximately said proximal end to approximately said distal end of said endotracheal tube;
    said suctioning tube being connectable to a vacuum source from the proximal end of said endotracheal tube, said suctioning tube terminating at one or more distally or inwardly facing holes located at or near the distal end of said endotracheal tube through which mucus can be suctioned before said mucus migrates up the inside walls of said endotracheal tube; and
    a cap with a proximal end and a distal end wherein said proximal cap end has an annular space into which the distal end of said endotracheal tube is received and wherein said distal cap end is perforated with a plurality of holes.

2. The mucus cleaning endotracheal tube of claim 1 wherein said distal cap end holes number between 2 and 8 and is each less than 1 millimeter in diameter.

3. The mucus cleaning endotracheal tube of claim 1 wherein said suction tube terminates with a hole at the distal end of said endotracheal tube and an annular space gap is left between the distal end of said endotracheal tube and the distal end of said cap.

* * * * *